(12) United States Patent
Brignac

(10) Patent No.: US 8,813,567 B2
(45) Date of Patent: *Aug. 26, 2014

(54) LOW PROFILE ULTRASOUND INSPECTION SCANNER

(71) Applicant: ALSTOM Technology Ltd, Baden (CH)

(72) Inventor: Jacques L. Brignac, Simsbury, CT (US)

(73) Assignee: ALSTOM Technology Ltd, Baden (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/709,668

(22) Filed: Dec. 10, 2012

(65) Prior Publication Data

US 2013/0091951 A1  Apr. 18, 2013

Related U.S. Application Data

(63) Continuation of application No. 12/398,704, filed on Mar. 5, 2009, now Pat. No. 8,347,724.

(51) Int. Cl.
*G01N 29/04* (2006.01)

(52) U.S. Cl.
USPC .................................. 73/625; 73/639; 73/618

(58) Field of Classification Search
USPC ............................................................ 73/625
See application file for complete search history.

(56) References Cited

U.S. PATENT DOCUMENTS

| 3,844,164 | A | 10/1974 | Romere |
| 5,062,301 | A | 11/1991 | Aleshin et al. |
| 5,619,423 | A | 4/1997 | Scrantz |
| 6,748,808 | B2 | 6/2004 | Lam et al. |
| 8,347,724 | B2 * | 1/2013 | Brignac ................. 73/639 |
| 2003/0188589 | A1 | 10/2003 | Harthorn et al. |

FOREIGN PATENT DOCUMENTS

| JP | 62-9268 | 1/1987 |
| JP | 62-192655 | 8/1987 |
| JP | 01-119759 | 5/1989 |
| JP | 2008-249510 | 10/2008 |

OTHER PUBLICATIONS

PCT International Search Report and the Written Opinion of the International Searching Authority, dated Jul. 12, 2010 (PCT/US2010/020960).

* cited by examiner

*Primary Examiner* — Hezron E Williams
*Assistant Examiner* — Gregory J Redmann

(57) ABSTRACT

An inspection scanner [1000] is described that has a low profile construction designed to fit into tight spaces and inspect structures [10] such as weld joints [13]. Wheel frame assemblies [1100, 1200] carry a probe holder assembly [1110] with an ultrasonic (US) array [1400] that emits US beams through the structure [10] and receives reflected sound waves. The probe holder assembly [1110] extends and US beam is angled away to inspect in tight locations. The wheel frame assemblies [1100, 1200] roll on wheels [1140, 1240] that drive an encoder [1250]. Encoder [1250] provides the specific locations for the received sound waves with respect to the weld. The locations and received sound waves are used to reconstruct a signal showing imperfections inside of structure [10]. The wheels [1140, 1240] may be magnetic to hold it to the structure [10] being inspected. A brake system [1600] may be employed to hold the inspection scanner [1000] at a given location.

15 Claims, 5 Drawing Sheets

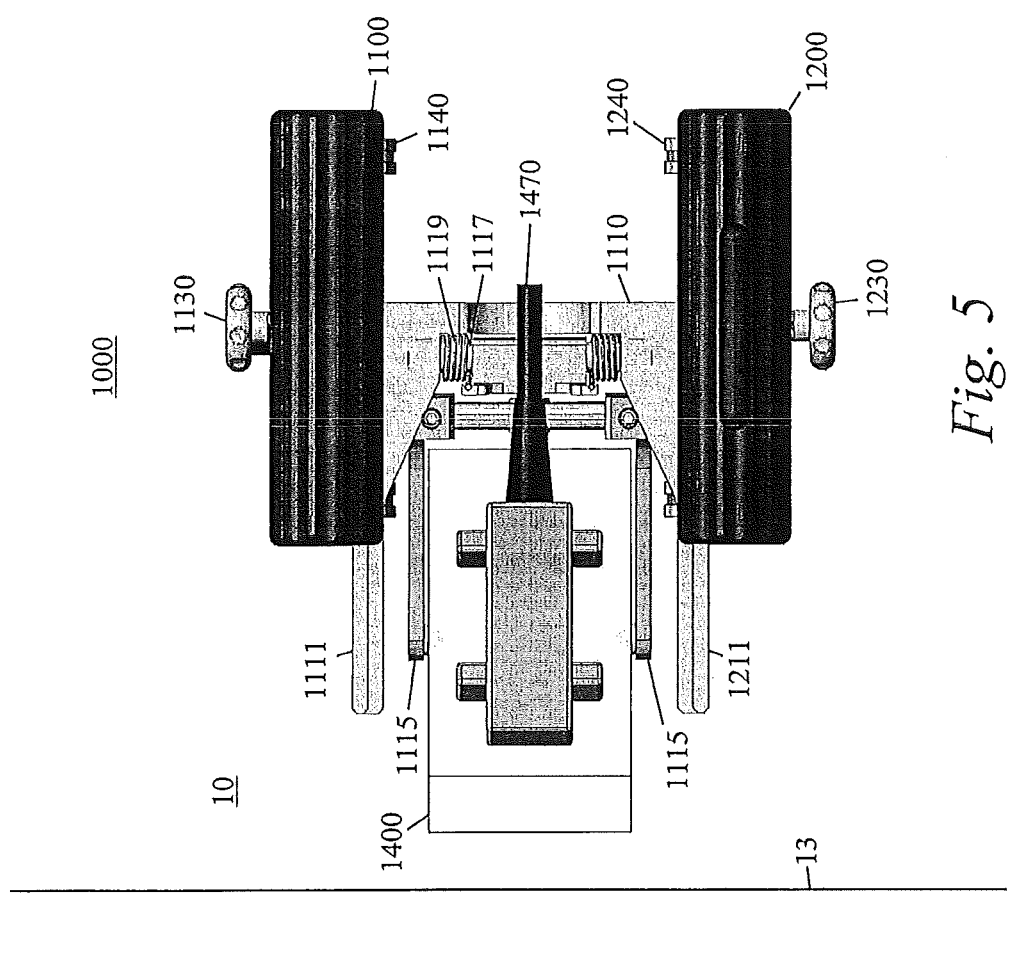

LOW PROFILE ULTRASOUND INSPECTION SCANNER

CROSS REFERENCE TO RELATED APPLICATION

This application is a Continuation of U.S. patent application Ser. No. 12/398,704, filed Mar. 5, 2009, the contents of which is incorporated by reference herein in its entirety.

TECHNICAL FIELD

The present disclosure relates to a device for inspecting structures using ultrasound and more specifically, for a low profile device for inspecting structures using ultrasound in spaces with little clearance.

BACKGROUND

Testing of pressure parts and various structures using nondestructive testing techniques is an arduous task, particularly when testing seam welds. For example, a boiler system having multiple components in a fixed, limited amount of space may be difficult to inspect with precision. Typically, using ultrasonic techniques (UT), an operator manually scans the desired area of the structure with a hand-held UT probe that delivers signals (sound waves) through the structure and weld and receives feedback measurements as a result of the scanning. Clearly such a manual process is susceptible to inaccuracies, since a human operator's fine motor skills while traversing the structure, may not be entirely stable or consistent, which translates to less than optimal readings (e.g., missed cracks or wall degradation, false positives, and other such errors).

Since damage and failure typically begins at a weld seam of these components, it is important to inspect the welds periodically. Since the components being inspected are part of a function system, it is best to inspect them without having to remove a component, or disassemble the system.

Commonly used inspection devices have employed ultrasonic scanners that were moved manually from place to place. The resulting readings are graphed or otherwise displayed to the operator to indicate the location of flaws. A scanner that delivers a probe that can quickly non-intrusively assess the condition of a weld decreases servicing time and is valuable.

General-purpose mechanical scanners were used for inspecting the condition of welds on various shaped objects. Due to their general-purpose nature, they tended to be large and bulky.

In steam generation systems, there typically are welded structures pipes that carry pressurized steam. These employ welds that must be monitored periodically. Due to the tight clearances, conventional inspection devices will not fit and are not adapted to the shape.

What is needed, therefore, is a low profile inspection device that can fit into tight spaces to inspect welds of components requiring frequent inspection.

SUMMARY

According to the aspects illustrated herein, there is provided an ultrasonic probe carrier includes an inspection scanner [1000] having a lower profile that prior art designs, for transmitting and receiving ultrasound beams for inspecting a volume of a structure [10] comprising:

at least one wheel frame [1100];

a ultrasound (US) array [1400] adapted to scan said volume of said structure [10] with ultrasonic beams angled away from said wheel frame [1100] and to receive ultrasound signals reflected back to the array [1400], the array [1400] attached to, and carried by wheel frame [1100];

wheels [1140] attached to the wheel frame [1100] for carrying the wheel frame [1100], the wheels [1140] allowed to rotate moving the frame in a forward direction or a reverse direction, along a surface of said structure [10];

an encoder [1250] adapted to monitor rotation of the wheels [1140] and location on said structure [10], and adapted to send an encoder signal corresponding to the received ultrasound signals such that each received ultrasound signal is identified with a location of said US array [1400] on said structure [10].

OBJECTS OF THE INVENTION

It is an object of the present invention to provide an ultrasound inspection scanner that is specially adapted to power generation equipment.

It is another object of the present invention to provide an ultrasound inspection scanner and acquisition system that can view various portions of a weld from a given location.

It is another object of the present invention to provide an ultrasound inspection scanner that is portable.

It is another object of the present invention to provide an ultrasound inspection scanner that is specially designed to inspect welds of a curved surface having various diameters.

It is another object of the present invention to provide an ultrasound inspection scanner that is specially designed to inspect welds of flat surfaces.

BRIEF DESCRIPTION OF THE DRAWINGS

Referring now to the figures, which are exemplary embodiments, and wherein the like elements are numbered alike:

FIG. 5 is a plan view of the embodiment of the inspection scanner of FIGS. 2, 3 and 4, as viewed from above.

DETAILED DESCRIPTION

Figure 1:
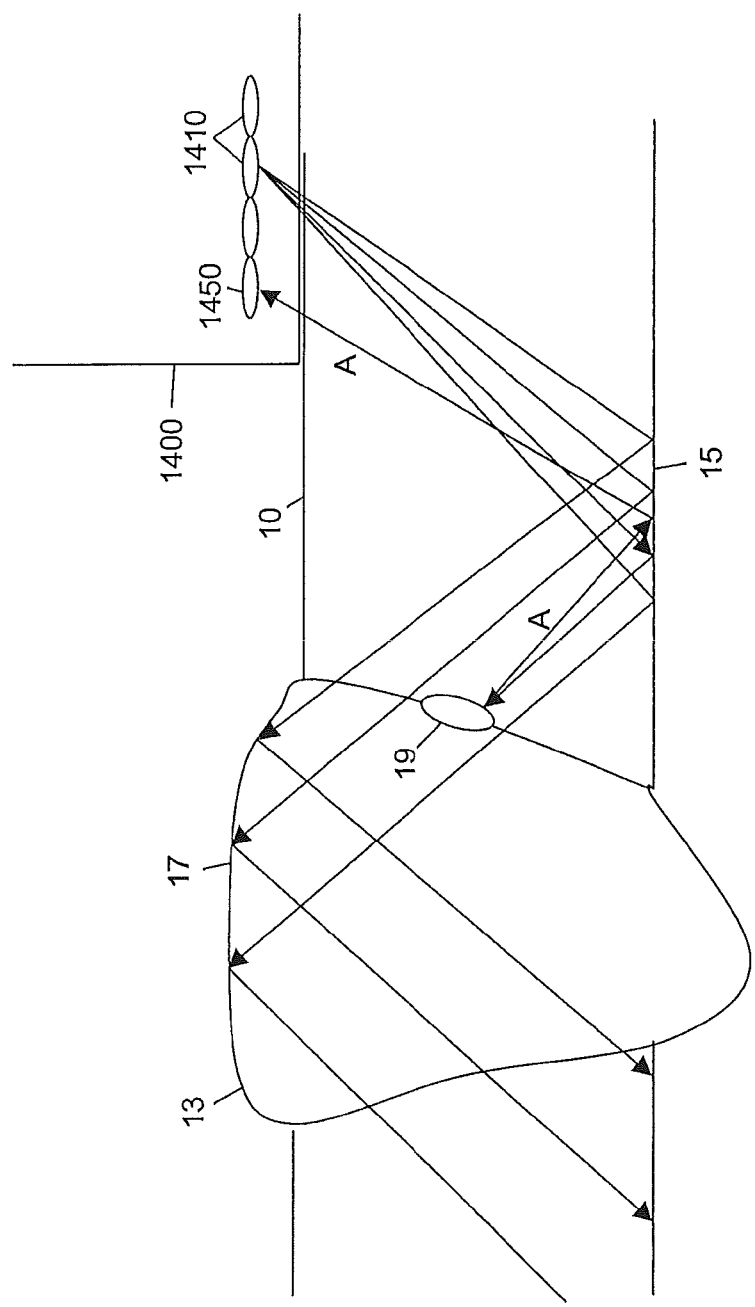
FIG. 1 is an illustration of the imaging geometry employed by the present invention.

An ultrasonic inspection system ("system") for providing nondestructive testing of pipe and piping welds having restricted or limited space therebetween is provided. The system includes an ultrasonic probe carrier having a low profile that enables the system to access tubes and welds having limited or restricted space among them.

Theory

Weaknesses in metal structures can be caused as a result of repeated mechanical forces acting on the structure, due to deterioration of from rust and corrosion, or due to improper initial construction. This applies especially to welds joints of metal structures, which ten to fail first.

These weaknesses may eventually cause a failure of a component. In the case of high-pressure components, failures may lead to catastrophic consequences.

Inspection and monitoring can identify these weaknesses before they can cause a problem. Once weakened components are identified, they may be replaced before there are safety issues and/or additional damage.

One specific use would be the closure weld to a turbine casing. Using conventional tools, it is very difficult, time-consuming and inaccurate to monitor this critical weld.

Since this is a critical weld and the turbine casing and experiences significant forces, it must be inspected frequently. As stated above, conventional inspection devices are difficult to use for this specific geometry and cramped spaces.

When these turbines are not functioning for maintenance, there are considerable lost production costs. For example, if a turbine were being used to create electric power for a utility company, the utility company would have to buy power from the grid during maintenance of their turbine casing. The electricity purchased from the grid is much more expensive that that produced by the turbine, and can become quite costly for longer maintenance periods. Therefore, a device specially made to inspect turbine piping welds accurately and quickly would result in significant cost savings for the utility companies.

Similar welds exist on many turbines and many have the similar shapes. These all experience considerable operating forces, and each requiring frequent inspections. Therefore, the low profile inspection device designed to efficiently and accurately inspect welds in cramped spaces would be very valuable to those who inspect these turbines.

There are many welds that are critical that have to be periodically inspected. Some of these are located in crowded locations with little open space. It is very difficult to use conventional inspection devices based upon their size and also they method of acquiring an image. Since many of these prior art devices inspect directly below the device, they cannot fit, and cannot be used.

Angled Beam

The present invention is specially adapted to inspect weld joint in crowded and cramped locations. This is accomplished by employing a low profile design, having an adjustable probe and having the ability to inspect volumes that are spaced away from it. It employs a beam angled away from the device to acquire inspection data. This device employs angled internal reflection geometry to acquire its data. Therefore, the device need not be directly above the portion to be inspected, but merely adjacent to it. This greatly facilitates data acquisition in tight spaces.

FIG. 1 shows angled beam geometry employed in the present invention. Ultrasound (US) beams, illustrated by arrows radiating from US array 1400, are transmitted from a plurality of transmitters 1410 of US array 1400. The US array 1400 employs phased array technology such that the direction of the US beam may be changed by altering the relative transmit power of the transmitters 1410. For simplicity, this is shown in FIG. 1 as a plurality of single beams from a single transmitter 1410.

The US beams are passed through structure 10 to a first interface 15. This interface is the structure's inside surface and the internal space. This interface may be a metal/gas or metal/liquid boundary that reflects the US beam. Most of the US beams then pass through the metal weld 13 to a second interface 17. Second interface is between the outside surface of structure 10 and the space above structure 10.

Portions of the incident US beam, hit an object 19, which may be a gap in the weld, or other material that has an ultrasound conductance significantly different from that of pure metal. Portions of the US beam are reflected back as indicated by the arrows marked "A". These reflected US rays reflect off of interface 15 and back to receiver 1450 of US array 1400.

Image Reconstruction

The US beam is received by the receivers 1450 in US array 1400 is then sent to a controller for processing. The controller has previously been updated with the geometry of structure 10 being analyzed. It collects the reflected US signals from receivers 1450 and reconstructs and image of objects internal to structure 10. Since interfaces between solid metal and other less dense objects create images; air bubbles, corrosion and other features may be easily identified in the reconstructed image. This image reconstruction may be performed by conventional image known methods.

Figure 2:
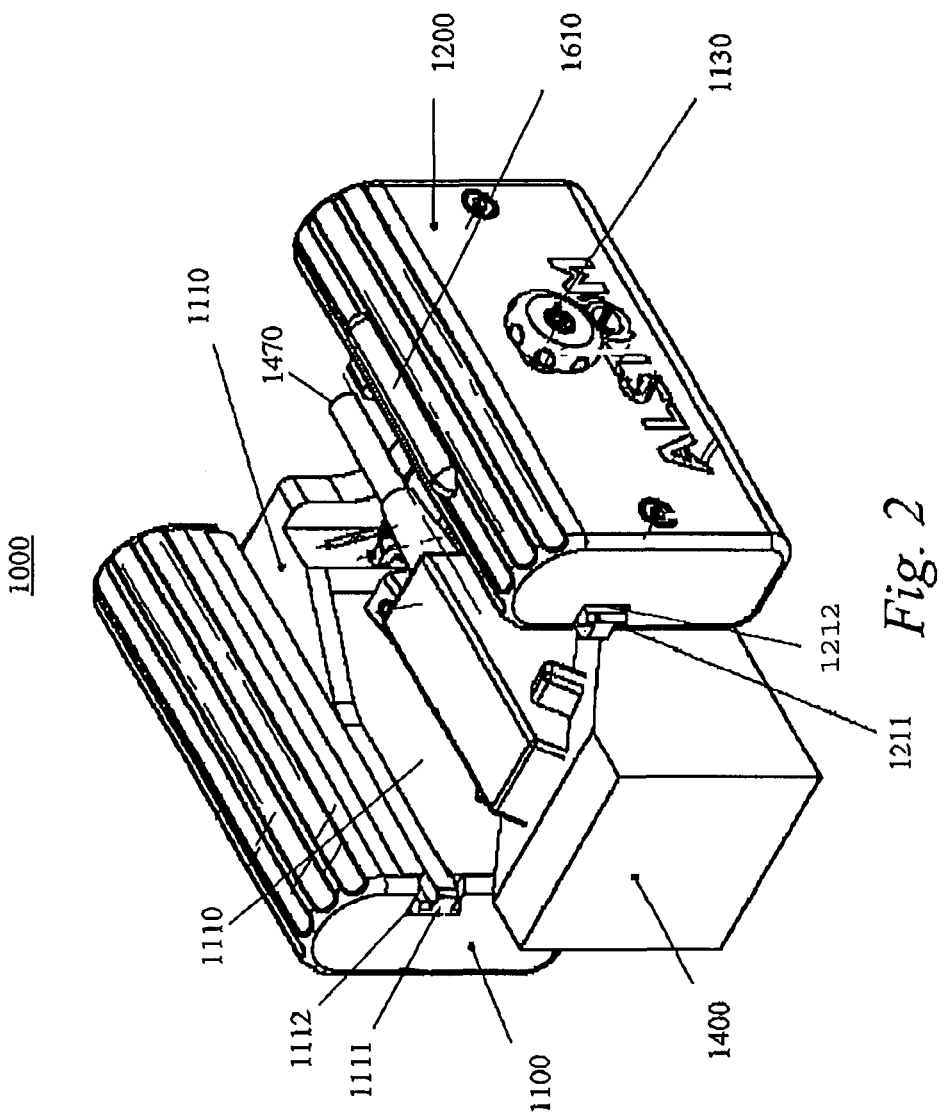
FIG. 2 is a perspective view of a low profile ultrasound inspection device according to one embodiment of the present invention.

FIG. 2 is a perspective view of an inspection scanner 1000 according to one embodiment of the present invention. This employs a low profile. Smaller is better when it comes to performing inspections in tight places. However, the inspection device must be large enough to be easily manipulated. It was found that most turbine closure welds had clearances of regions to be inspected to be about 3 inches. Therefore, a device having a profile of less than 3 inches would be useful.

Figure 3:
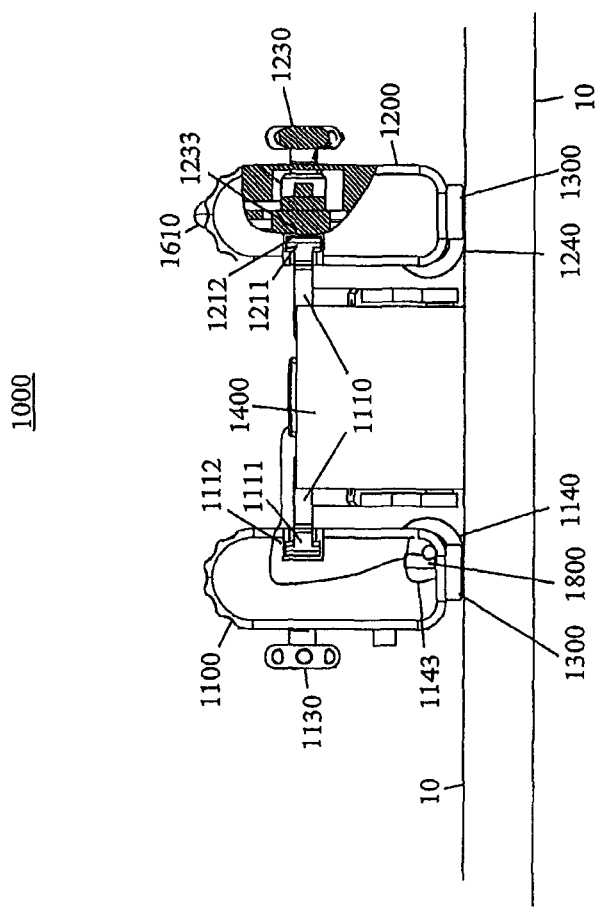
FIG. 3 is a partial cut-away elevational view of the rear of the embodiment of the inspection scanner of FIG. 2.

Wheel frame assemblies 1100, 1200 roll on wheels (1140, 1240) of FIG. 3). Wheel frame assemblies 1100, 1200 are connected by a probe holder assembly 1110.

Probe holder assembly 1110 has slides 1111 and 1211 that ride in slide slots 1112, 1212 of wheel frame assemblies 1100, 1200, respectively.

At least one locking knob 1130 may be tightened to secure slide 1211 to probe holder at an adjustable position relative to wheel frame assembly 1200. A similar arrangement exists with wheel frame assembly 1100 that is not shown from this view.

An optional brake button 1610 is employed to stop the wheels (1240 of FIG. 3) to keep the device at its current location.

Probe holder assembly 1110 carries US array 1400. US array 1400 is a phase array of ultrasonic transducers that can direct an ultrasonic beam at various angles based upon the relative power of each of its transmitters (1410 of FIG. 1). This allows the US beams to scan through a volume of a structure 10 intended to be inspected. US array 1400 also has receivers (1450 of FIG. 1) that receive reflected US signals.

The scanning method allows for a thorough inspection of structure throughout its volume to its far surfaces. This would detect not only imperfections within the volume of the structure 10, but also will detect corrosion near the surfaces.

Signals received by US array 1400 are passed through signal cable 1470 to a processing device that reconstructs images from the sensed signals.

FIG. 3 is a partial cut-away elevational view of the rear of the embodiment of the inspection scanner of FIG. 2. It can be seen here that wheel frame assemblies 1100, 1200 roll on wheels 1140, 1240 on the surface of structure 10. Structure 10 is a metal structure that has a weld 13 intended to be inspected.

Preferably, wheels 1140, 1240 may be magnetized to hold wheel frame assemblies 1100, 1200 to structure 10 while weld 13 is being inspected. Alternatively, there may be a magnetic device 1300 employed on inspection scanner 1000. In still another alternative embodiment, the user may simply hold the present invention to structure 10 for inspection of weld 13.

US array 1400 is carried by probe holder arms 1115. Probe older arms are part of probe holder assembly 1110. Probe holder arms 1115 allow US array 1400 to drop down and ride along the outer surface of structure 10.

Probe holder assembly 1110 has slides 1111, 1211 that slide along slide slots, 1112, 1212, respectively to allow US array 1400 to extend to the side of the center of inspection scanner 1000. Once positioned, locking knob 1230, that may be a screw, is tightened to press side clamp pad 1233 against slide 1211 to fix the position of wheel frame assembly 1200 with respect to probe holder assembly 1110 and US array 1400.

Locking knob 1130 performs the same function with respect to wheel frame assembly 1100. Brake button 1610 operates a brake that stops wheels 1240 causing inspection scanner 1000 to remain at the current location on structure 10 when activated.

Figure 4:
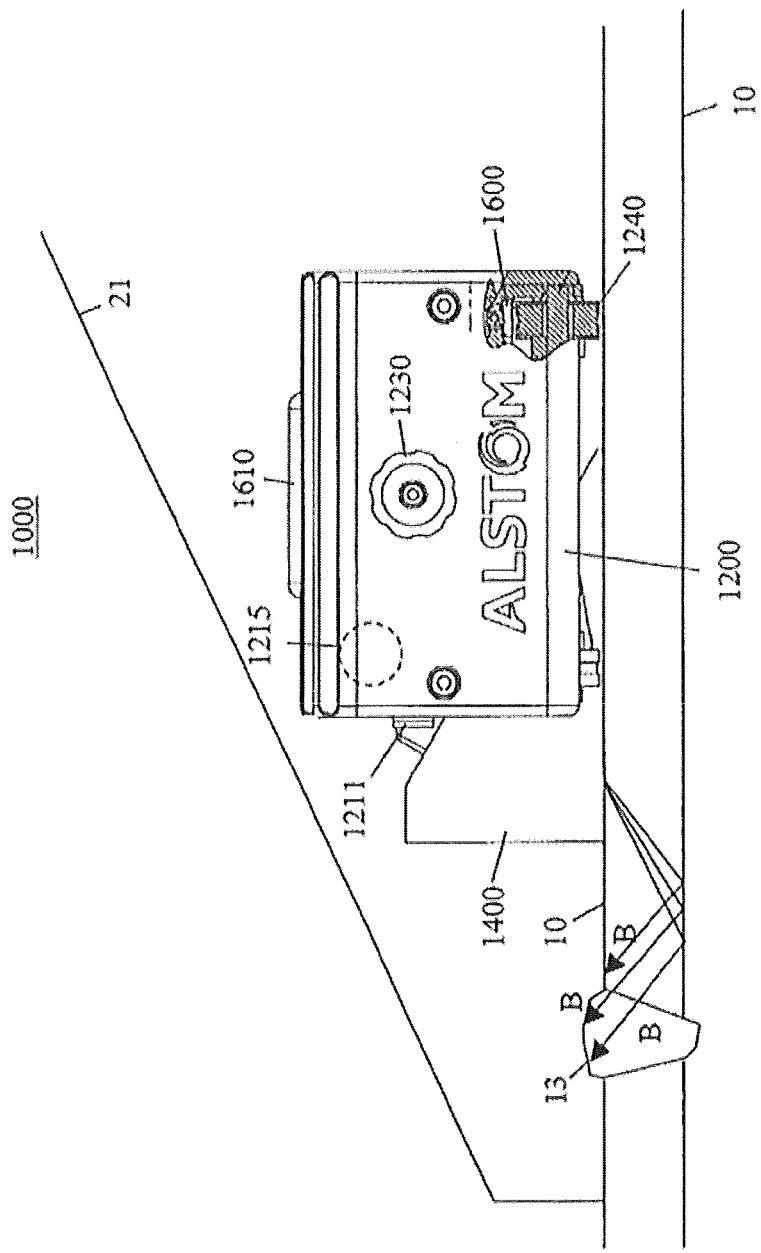
FIG. 4 is a side elevational view of the embodiment of the inspection scanner of FIGS. 2 and 3.

FIG. 4 is an elevational view of the embodiment of the inspection scanner of FIGS. 2 and 3 as viewed from the rear. An obstruction 21 makes it difficult for a conventional inspection device to inspect weld 13 on structure 10. Usually, they are significantly higher than the present invention. Also, prior art devices had to be above the portion intended to be inspected since they aimed their inspection beam downward. Prior art devices also did not employ an adjustable structure allowing their transducers to move closer to the area to be inspected than the carrying device.

It can be seen how the low profile (low height) design of the present invention fits under the obstruction 21. In addition, US array 1400 is shown extended in this figure toward weld 13. The locking knob 1230 clamps against slide 1211 when screwed in to keep array 1400 in a given position.

Also, US array 1400 transmits its beams in an outward angled directed toward weld 13, as shown by the arrows marked "B". This further extends the reach of the present invention into cramped spaces.

A brake member 1600 is shown which presses against wheel 1240 to hold inspection scanner 1000 in place when brake button 1610 is activated.

FIG. 5 is a plan view of the embodiment of the inspection scanner of FIGS. 2, 3 and 4, as viewed from above. FIG. 5 shows the US array 1400 carried by a pair of probe holder arms 1115. These are pivotally attached at carrier pivot 1117 to the probe holder assembly 1110. A spring 1119 urges US array 1400 to make contact with structure 10.

In this embodiment, probe holder assembly 1110 is allowed to slide relative to wheel frame assemblies 1100, 1200 in a direction perpendicular to the direction in which wheels 1140, 1240 are rolling the device. In this figure, probe holder assembly 1110 is extended to the left side of frame 1100. This allows US array 1400 to extend into smaller, more cramped spaces. Also, due to the transmission geometry of US array 1400, the US beam is directed even further to the left of US array 1400, further into cramped spaces.

In alternative uses, the inspection scanner may fit into the location intended to be scanned, however, a user may not physically extend their arm in to reach the inspection scanner 1000. In this case, and alternative embodiment would be useful. If the inspection scanner 1000 had a wheel motor (shown in phantom in FIG. 3 as 1143), it could attach to the structure 10, and then wheel itself around the structure held on by the magnetic wheels 1140, 1240. All that would be required to control the wheel motor would be a signal transmitted to it, possibly by radio link, from a controller operated by the user.

Also, another alternative embodiment would include a slide motor (shown in phantom as 1215 in FIG. 4). Slide motor 1215 would operate on slide 1211 to extend or retract probe holder assembly (1010 of FIG. 5) and US array 1400. The slide motor may be controlled through a radio link to a controller operated by a user.

Although the invention has been described and illustrated with respect to exemplary embodiments thereof, it should be understood by those skilled in the art that the foregoing and various other changes, omissions and additions may be made therein and thereto, without parting from the spirit and scope of the present invention. Accordingly, other embodiments are within the scope of the following claims.

What is claimed is:

1. An inspection scanner having a lower profile that prior art designs, for transmitting and receiving ultrasound beams for inspecting a volume of a structure comprising:
    at least one wheel frame;
    a ultrasound (US) array adapted to scan said volume of said structure with ultrasonic beams angled away from said wheel frame and to receive ultrasound signals reflected back to the array, the array attached to, and carried by wheel frame;
    wheels attached to the wheel frame for carrying the wheel frame, the wheels allowed to rotate moving the frame in a forward direction or a reverse direction, along a surface of said structure;
    a brake to lock the wheels in place;
    an encoder adapted to monitor rotation of the wheels and location on said structure, and adapted to send an encoder signal corresponding to the received ultrasound signals such that each received ultrasound signal is identified with a location of said US array on said structure.

2. The inspection scanner of claim 1, further comprising:
    a probe holder assembly adapted to be adjustable for carrying the US array, the probe holder assembly moveable to extend the US array to various locations without requiring the wheel frame to be moved, thereby adjusting volume of structure to be inspected.

3. The inspection scanner of claim 1, wherein the wheels are magnetized to hold the inspection scanner to said structure.

4. The inspection scanner of claim 1, further comprising a magnetic device to hold the inspection scanner to said structure.

5. The inspection scanner of claim 1, wherein the US array has a plurality of transmitters adapted to each transmit an adjustable amount of ultrasound power to direct the ultrasound beam in a desired direction to scan the weld.

6. The inspection scanner of claim 1, wherein:
    the inspection scanner has a maximum height of 3 inches.

7. The inspection scanner of claim 1, further comprising:
    a wheel motor coupled to the wheels for operating the wheels moving the inspection scanner when a signal is received from a remote controller.

8. The inspection scanner of claim 1, further comprising:
    a slide motor coupled to the probe holder assembly causing it to position the US array at a different location when a signal is received from a remote controller.

9. An inspection scanner having a lower profile than prior art scanners for inspecting a volume of a structure comprising:
    a front wheel frame;
    a rear wheel frame;
    a probe holder assembly having a pair of slides extending along its sides, each slide being received by slide slots of the front wheel frame and the rear wheel frame, respectively, the probe holder assembly being allowed to slide with respect to the wheel frames;
    a ultrasound (US) array adapted to scan said volume of said structure with ultrasonic beams angled away from said probe holder assembly;

wheels attached to the wheel frames allowed to rotate moving the inspection scanner in a forward direction or a reverse direction along said structure;

a brake to lock the wheels in place;

an encoder adapted to monitor rotation of the wheels and location on said structure, and adapted to send an encoder signal corresponding to the received ultrasound signals such that each received ultrasound signal is identified with a location of said US array on said structure.

10. The inspection scanner of claim 9, wherein:
the inspection scanner has a maximum height of 3 inches.

11. The inspection scanner of claim 9 wherein the US array is pivotally attached to the probe holder assembly and is urged against said structure by an urging device.

12. The inspection scanner of claim 11 wherein the urging device is a spring.

13. The inspection scanner of claim 9, further comprising:
a wheel motor coupled to the wheels for operating the wheels moving the inspection scanner when a signal is received from a remote controller.

14. The inspection scanner of claim 9, further comprising:
a slide motor coupled to the probe holder assembly causing it to position the US array at a different location when a signal is received from a remote controller.

15. The inspection scanner of claim 9, wherein the US array has a plurality of transmitters adapted to each transmit an adjustable amount of ultrasound power to direct the ultrasound beam in a desired direction to scan said volume of said structure.

* * * * *